(12) United States Patent
Irnich (10) Patent No.: US 6,480,738 B2
(45) Date of Patent: Nov. 12, 2002

(54) DEFIBRILLATOR WITH MEANS FOR PRODUCING DEFIBRILLATION PULSES WITH AT LEAST TWO CAPACITORS IN DIFFERENT CONFIGURATIONS AND METHOD OF USE

(76) Inventor: Werner Irnich, Birkenweg 60, D-35435 Wettenberg (DE)

( * ) Notice: Subject to any disclaimer, the term of this patent is extended or adjusted under 35 U.S.C. 154(b) by 0 days.

(21) Appl. No.: 09/879,862

(22) Filed: Jun. 12, 2001

(65) Prior Publication Data

US 2002/0049473 A1 Apr. 25, 2002

(30) Foreign Application Priority Data

Jun. 14, 2000 (DE) .......................................... 100 29 112

(51) Int. Cl.$^7$ ................................................. A61N 1/39
(52) U.S. Cl. ............................................................. 607/5
(58) Field of Search ............................... 607/5, 6, 7, 8, 607/4

(56) References Cited

U.S. PATENT DOCUMENTS

| | | |
|---|---|---|
| 5,507,781 A | 4/1996 | Kroll |
| 5,540,721 A | 7/1996 | Kroll |
| 5,991,658 A | 11/1999 | Brewer |
| 6,047,211 A | 4/2000 | Swanson |

FOREIGN PATENT DOCUMENTS

| | | |
|---|---|---|
| EP | 0 515 059 A1 | 11/1992 |

OTHER PUBLICATIONS

Hamzei, et al, "Three Capacitor Multi–step Waveform Lowers Defibrillation Threshold ," Pace, vol. 5 ( No. II), ( Jun. 11, 1999).

Irnich, W., "The Fundamental Law of Electrostimulation and its Application to Defibrillation," Pace, p. 1433–47, (Nov. 11, 1990).

Irnich, W., "Optimal Truncation of Defibrillation Pulses," Pace, p. 673–88, ( Apr. 11, 1995).

Natale, et al., "Relative Efficacy of Different Tilts with Biphasic Defibrillation in Humans," Pace, p. 197–206, (Feb. 11, 1996).

Hahn, et al., "Optimization of 90 microfarad Biphasic Defibrillation Waveforms for ICDs Using a Theoretical Model and Central Composite Design of Experiments," Pace.

Schauerte, et al, "Optimized Pulse Durations Minimize the Effect of Polarity Reversal on Defibrillation Efficacy with Biphasic Shocks," Pace, p. 790–7, ( May 11, 1999).

Cleland, "A Conceptual Basis for Defibrillation Waveforms," Pace, p. 1186–95, ( Aug. 11, 1996).

Kroll, "A Minimal Model of the Monophasic Defibrillation Pulse," Pace, p. 769–77, ( Apr. 11, 1993).

Irnich, W., "Letter to the Editor on Optimization of Defibrilllation pulses," Pace, p. 1271–2, ( Aug. 11, 1995).

Sra, et al., "The Effect of Biphasic Waveform Tilt in Transvenous Atrial Defibrillation ," Pace, p. 1613–8, ( Jun. 11, 1997).

Irnich, W., "Letter to the editor responding to the Pace 1997; 20:1613–8 article," Pace, p. 3014, ( Dec. 11, 1997).

*Primary Examiner*—Scott M. Getzow
(74) *Attorney, Agent, or Firm*—Hahn Loeser + Parks LLP; Stephen L. Grant (57) ABSTRACT

A defibrillator for atrium and/or ventricle having at least two capacitors which in the production of defibrillation pulses are discharged in at least two phases in succession in different configurations, wherein there are provided switching means which control the discharge in the at least two discharge phases in such a way that the mean value of their voltages is substantially equal and no voltages below the rheobase occur in any of the discharge phases, and a corresponding defibrillation method.

22 Claims, 6 Drawing Sheets

FIGURE 1: Defibrillation input

FIGURE 3: RC1 and RC2 at 30% tilt

DEFIBRILLATOR WITH MEANS FOR PRODUCING DEFIBRILLATION PULSES WITH AT LEAST TWO CAPACITORS IN DIFFERENT CONFIGURATIONS AND METHOD OF USE

The invention relates to a cardiac defibrillator, particularly an implantable one, of the kind set forth in claim 1 and a corresponding method.

BACKGROUND OF THE ART

Defibrillators of this kind are known from sources such as European Pat. application No. 0 515 059. Defibrillators are generally implanted in increasing numbers in the case of patients who repeatedly suffer from fibrillation which requires electrotherapeutic help. To provide assistance without the presence of a doctor—more specifically because in many cases the doctor would not be on hand sufficiently quickly—nowadays defibrillators of that kind are already being implanted in relatively large numbers and are thus available to the patient at any time. To keep down the size of those units while still providing sufficient energy even for repeated defibrillation procedures, optimum utilization of energy during an individual defibrillation procedure is a particularly important consideration.

The previously known defibrillator admittedly includes a plurality of capacitors which can be switched in different configurations. A disadvantage in that respect however that no indications whatsoever in regard to the sequence and the times of switching over the capacitors for optimization of the energy demand in a defibrillator of that kind are known. In this connection attention is directed to the following literature which however also does not provide any more detailed indications in this respect. It represents a summary of the previous endeavors to provide information about the energy demand in connection with defibrillators:

1. Schudder J C, Stoeckle H, West J A, et al: Transthoracic ventricular defibrillation in the dog with truncated exponential stimuli. IEEE Trans Biomed Eng BME 1971; 18: 410–415
2. Hamzei A, Mouchavar G, Badelt St et al: Three-capacitor multistep waveform lowers defibrillation threshold. PACE 1999; 22(5, II): abstract #87
3. Irnich W: The fundamental law of electrostimulation and its application to defibrillation. PACE 1990; 13: 1433–1447
4. Irnich W: Optimal truncation of defibrillation pulses. PACE 1995; 18: 673–688
5. Natale A, Sra J, Krum D et al: Relative efficacy of different tilts with biphasic defibrillation in humans. PACE 1996; 19: 197–206
6. Hahn St J, Heil J E, Lin Y et al: Optimization of 90 $\mu F$ biphasic defibrillation waveform for ICDs using a theoretical model and central composite design of experiments. PACE
7. Schauerte P, Schöndube F A, Grossmann M et al: Optimized pulse duration minimizes the effect of polarity reversal on defibrillation efficacy with biphasic shocks. PACE 1999; 22: 790–797
8. Cleland B G: A conceptual basis for defibrillation waveforms. PACE 1996; 19: 1186–1195
9. Kroll M W: A minimal model of the monophasic defibrillation pulse. PACE 1993; 16: 769–777.

These references will be referred to hereinafter by these numbers.

Even these publications do not give any indications in regard to the stated problem, as will also be apparent from the systematic presentation hereinafter of the problems involved and the concept of the present invention.

SUMMARY OF THE INVENTION

An object of the present invention is to provide a defibrillator of the above-indicated kind or a corresponding defibrillation method, in which there are provided automatic control means which optimize the defibrillation effect with a plurality of capacitors.

The object is attained by the features recited in claim 1.

The object of the invention is attained by realizing that the degree of efficiency $\eta$ (also referred to as "eta") of the defibrillator in the various discharging procedures must be optimized in each case in such a way that the overall effect is also an optimum. The term $\eta$ is used in electrical engineering to mean the "efficiency" which normally defines the ratio of useful to applied energy. That consideration is based on an "input"- to "output"-comparison which in the case of the defibrillator would have to be such that the energy taken from the battery is compared to the energy delivered to the heart. Here however the notion of efficiency is additionally expanded in such a way that it embraces more than a straightforward input-output calculation, but also includes the question of the biological effectiveness of different pulse shapes.

The problem involved can be illustrated by reference to two examples: A favorable input-output ratio would be achieved in defibrillation if the output capacitor or capacitors was or were completely discharged. The efficiency would be 1. However Schudder et al (Ref. 1) already found in 1970 that the effectiveness is increased if the capacitor or capacitors is or are not completely discharged, but the discharge procedure is prematurely interrupted (truncated or curtailed). Now, it is worth noting that the optimum "tilt" (this English expression to denote slope or gradient is an established part of defibrillator terminology, and it should better be referred to as "degree of utilization") has not hitherto been systematically investigated. On the contrary, the electrophysiological problem was made more complicated by the fact it was postulated as being self-evident that the optimum "tilt", once found, enjoyed general applicability. However the engineers of the defibrillator manufacturer which for a long time was the only one prejudiced the discussion about optimum tilt by virtue of the fact that they implemented the idea which from the point of view of electrical engineering appears a reasonable one of providing for discharge of the output capacitor or capacitors to 20% of the initial voltage (corresponding thereto is a degree of utilization or tilt of 80%), to which there corresponds an efficiency of 96% (as the residual voltage is involved in quadratic terms in the energy calculation). That assumption was not derived from any defibrillation experiments but was based on purely electrical engineering considerations.

As a second example mention may be made of a poster (Ref. 2) which was displayed in Toronto, Canada, in May 1999, on the occasion of the NASPE-Conference. The authors reported that, by virtue of serial connection of three output capacitors previously discharged to about 85%, they had required a lesser amount of stored energy in comparison to just one capacitor which was discharged to 45%. They explained that increased efficiency on the basis that a pulse with a rising pulse shape is more desirable, on the basis of the "membrane-response-model" hypothesis thereof. That interpretation cannot be reconciled with the basic law of electrostimulation which is also applicable in regard to defibrillation (Refs. 3, 4). The fact that nonetheless a first parallel and then a serial discharge can be advantageous involves reasons related to electrical engineering, which will be discussed in greater detail hereinafter.

According to the present invention, however, a superior defibrillator is provided compared to the known defibrillators. When ascertaining the tilt or the normalized residual voltage in the discharge procedure in the prior art, measurements were made directly on the patient and which thus best correspond to the prevailing factors by virtue of the fact that the residual voltage is adapted to the defibrillation impedance upon discharge or in terms of tilt.

In this respect consideration was given inter alia to the fact that stimulation and defibrillation obey the law which was already published in 1909 by Lapicque and which can be formulated as follows:

$$U(mean) = U_{rheobase}(1 + T_{chronaxie}/T) \quad (1)$$

wherein:

U(mean)=mean voltage during a stimulation pulse, $U_{rheobase}$=the voltage which just still stimulates with an infinitely long pulse duration (a more theoretical value), $T_{chronaxie}$=pulse duration at double the rheobase value.

The present invention is based upon the realization that two rules apply in regard to the effect of defibrillation as a function of the pulse duration:

the voltage-time integral which increases linearly with the pulse duration is decisive, and the pulse worsens the defibrillation effect if it falls below a given value, the above-mentioned "rheobase" value.

Accordingly, it is further concluded therefrom that two pulses of different shape achieve the same effect if the mean value of their voltage is equal and none of the pulses has components below the rheobase. It can be mathematically deduced that, in an exponential procedure, the mean value can be correspondingly calculated as follows:

$$U(mean) = (U(o) - U(residue)):ln(U(o)/U(residue)) \quad (2)$$

wherein:

U(o)=initial voltage to which the capacitor was charged,

U(residue)=residual voltage at the end of the pulse which in accordance with the theory is identical to the rheobase value, that is to say $U(residue) = U_{rheobase}$ If the mean voltage is related to the initial value U(o), that affords a normalized mean voltage (NMV):

$$NMV = U(mean)/U(o) = (1 - U(residue)/U(o)):ln(U(o)/U(residue)) \quad (3)$$

The above-mentioned tilt is also determined from the values U(o) and U(residue), more specifically in accordance with equation (4):

$$tilt = 1 - U(residue)/U(o) \quad (4)$$

from which it is possible to deduce the following:

$$U(residue)/U(o) = 1 - tilt \quad (5)$$

and $$U(o)/U(residue) = 1:(1 - tilt) \quad (6)$$

Equation (3) can then be correspondingly written as follows:

$$NMV = tilt:ln(1:(1 - tilt)) \quad (7)$$

For all exponential discharge, that means that the mean value is always equal if only U(o) and U(residue) or tilt are equal.

Assuming that two partial capacitors are discharged first in parallel and then, after they have been discharged to a residual voltage U(residue), they are discharged by serial connection from double the residual voltage again to U(residue), the overall duration of the discharge process is equal to that of a single capacitor with the same initial and residual voltages U(o) and U(residue), and the following can be formulated:

$$U(residue) = U(o)exp(-t/RC), \text{ there from: } t = RC * ln(U(o):U(residue)) \quad (8)$$

For any ratio of U(residue):U(o), we obtain from a comparison of the time of the individual capacitor C1 to the total time of the two partial capacitors C2:

$$RC1\ ln(U(o):U(residue)) = RC2\ ln(U(o):U(residue)) + RC2\ ln(U(o):U(residue)) + \tfrac{1}{2}RC2\ ln\ 2 \quad (9)$$

Or, expressed with equation (6):

$$RC1\ ln(1:(1-tilt)) = RC2\ \{2\ ln(1:(1-tilt)) + 0.5\ ln2\} \quad (10)$$

with ln 2 in the terms at the right in (9) and (10) as the doubled residual voltage is again discharged to the residual voltage at half the capacitance.

A conditional equation for RC2 or for the ratio C2/C1 can be derived from equation (10), as follows:

$$RC2 = RC1\ ln(1:(1-tilt)):\{2\ ln(1:(1-tilt)) + 0.5\ ln\ 2\} \quad (11a)$$

$$C2/C1 = ln\ (1:(1-tilt)):\{2\ ln(1:(1-tilt)) + 0.5\ ln2\} \quad (11b)$$

In regard to the discharge of a single capacitor, it was deduced from the theory of defibrillation (Ref. 4) that a respective optimum tilt is associated with the capacitor. That makes the seemingly complicated replacement of U(o) and U(residue) by tilt—also in connection with the invention described herein—understandable; for, it can be directly looked up so that evaluation can be affected not only by calculation but directly also with a look-up table.

If it is formulated that the capacitors are to discharge to half the voltage, and the tilt is then 50%, equation (11a) simply gives as follows:

$$C2 = C1\ ln\ (1:(1-50\%)):\{2\ ln\ (1:(1-50\%)) + 0.5\ ln2\} = C1 \cdot 1:2.5 = 0.4C1 \quad (12)$$

As for the individual discharge processes of RC2 the same respective mean value is afforded in accordance with equation (2) and (7) respectively and as moreover the duration for both forms of discharge is identical in accordance with equation (9), both must also have the same defibrillation effect. What is of particular significance is the fact that the stored energy for both forms of discharge is different, with the same initial voltage:

$$E1 = 0.5 \cdot C1 \cdot U(o)^2 \text{ and } E2 = 0.5 \cdot 0.8 \cdot C1 \cdot U(o)^2 \quad (13)$$

and:

$$E2:E1 = 0.8 \quad (14)$$

Therefore the parallel/serial discharge needs 20% less energy to arrive at the same result. In that respect, it is immaterial whether the two capacitances are firstly discharged simultaneously parallel or sequentially, before they are then discharged serially.

All in all it is possible in that way with the features according to the invention for the moments in time and/or the sequence of switching over between different capacitor configurations in the discharge procedure to be ascertained in the optimum manner and for the appropriate switching operations to be correspondingly triggered.

According to the invention, therefore, a defibrillator for atrium and/or ventricle is provided with at least two output capacitors which upon defibrillation are discharged in at least two phases in succession in different configurations, wherein the discharge in the at least two discharge phases is controlled by suitable switching means in such a way that the mean value of their voltages is substantially equal and voltages below the rheobase do not occur in any of the discharge phases.

In this way it is possible also to achieve optimum defibrillation results in systems with multi-capacitor arrangements, while an additional degree of freedom in terms of dimensioning of defibrillators is achieved in that the most widely varying types of capacitors and arrangements can be used, as are appropriate for reasons of space or other optimization reasons and nonetheless optimum utilization of the available energy is made possible for those capacitors. In that fashion the defibrillators can provide their service for a very long period of time without re-implantation.

If there are provided further switching means which break off the discharge procedure in the first discharge phase in dependence on the ascertained discharge time constant —which is determined by the capacitor and the electrode resistance—upon the attainment of a predetermined tilt or the corresponding residual voltage or a discharge time duration which is to be expected and which is previously calculated on the basis of the ascertained time constant until attainment of the tilt or the corresponding residual voltage and which correspondingly continue the discharge in a second phase with a series connection of the capacitors with voltage doubling, the above-mentioned aim can be embodied with a circuit arrangement which is simple to carry into effect or with a corresponding software-controlled system.

If the first configuration involves switching means which control the discharge of a single capacitor, the discharge of two parallel-connected capacitors or the sequential discharge of two individual capacitors, the invention can be advantageously used in relation to various design configurations of defibrillators.

It is particularly advantageous if there are provided switching means which determine the discharge time constant in the first phase in the first configuration during the discharge so that it is possible in each case to have recourse to the value ascertained in that way in respect of the normalized residual voltage or tilt in subsequent discharge procedures for other capacitor configurations.

Desirably it is also possible to provide switching means which with predetermined impedance values, instead of a single-capacitor or multi-capacitor system, also activate the individual discharge of a capacitor (one-capacitor system) if that is desirable from the point of view of energy in particular cases.

As the residual voltage remaining on the capacitor after defibrillation in accordance with the above-mentioned principles generally cannot be "held" until a later defibrillation procedure occurs, it seems appropriate if there are provided switching means for subsequently discharging that residual voltage in inverted mode (as a bi-phase system). That is preferably effected in a parallel circuit configuration.

To permit individual adaptation to individual factors of the patient concerned in individual cases, it is advantageous if the ascertained tilt or the corresponding residual voltage is additionally variable by substantially plus/minus 20% as a function of the time constant RC1 or RC2.

Similar considerations apply in regard to the corresponding method claims.

BRIEF DESCRIPTION OF THE DRAWINGS

An advantageous embodiment of the present invention is described in greater detail hereinafter by the text, including a table, and the Figures in which.

DETAILED DESCRIPTION OF THE INVENTION

The advantage of using double capacitors will be set forth herein in relation to an advantageous embodiment of the invention. Here the advantages of the teaching according to the invention can be particularly clearly verified. If the efficiency is identified as the ratio of the delivered to the stored energy, it will be seen that the residual energy in the case of the parallel-serial connection only ever constitutes a quarter of that which is still stored on the individual capacitor. In the example with a tilt of 50% the efficiency is 75% in the case of the individual capacitor, whereas it is 93.75% in the case of the two partial capacitors. The lower initial energy (80%) is afforded by the lower residual energy (6.25%) of the two partial capacitors. The individual capacitor needs 1.25 times the energy in order to achieve the same effect.

Heretofore the approach by way of the degree of utilization (tilt) in the calculation in equation (11) gave a relative ratio between C1 and C2. If we ask which specific time constant RC1 is concealed behind a 50% tilt, attention is directed to Table 1 at the end of this detailed description. Specified therein for a tilt of 50% is an RC1 of between 6.4 and 6.6 ms, on average 6.5 ms, which with a defibrillation impedance of 50Ω gives a preferred capacitance for the capacitor C1 of 130 $\mu$F. The individual capacitor of the dual combination in accordance with equation (12) then has a capacitance of:

$$C2 = 0.4\ C1 = 52\ \mu F \qquad (15)$$

In accordance with the invention therefore when settling for a time constant on the basis of a look-up table (Table 1) it is possible to determine the corresponding value for the pulse duration, tilt and efficiency for the individual capacitor. The partial capacitor corresponding thereto can then be ascertained with equation (11), for the parallel-serial use. This and the parameters resulting therefrom are summarized in Table 1 from which it is possible to select the respective combination insofar as either the partial capacitor with an assumed load is predetermined, or a degree of efficiency which permits a large capacitor with at the same time a low voltage.

In the foregoing example of the energy calculation for a 50% tilt, it is possible to see that the levels of energy delivered are the same for both circuitry versions. That is due to the fact that the initial voltage and the mean voltage are equal for both versions. For a tilt of less than 50%, the series connection of the partial capacitors during the residual discharge means that a higher voltage is produced than during the first phase so that the overall mean value of the voltage is higher with two capacitors. As it is not the delivered energy but the time integral in relation to voltage that is the crucial parameter in terms of defibrillation, the initial voltage can be reduced when using the double capacitors to the amount by which the voltage mean values increase. For tilts of greater than 50%, the initial voltage in the case of the two-capacitor system will have to be set at a correspondingly higher level.

Figure 1:
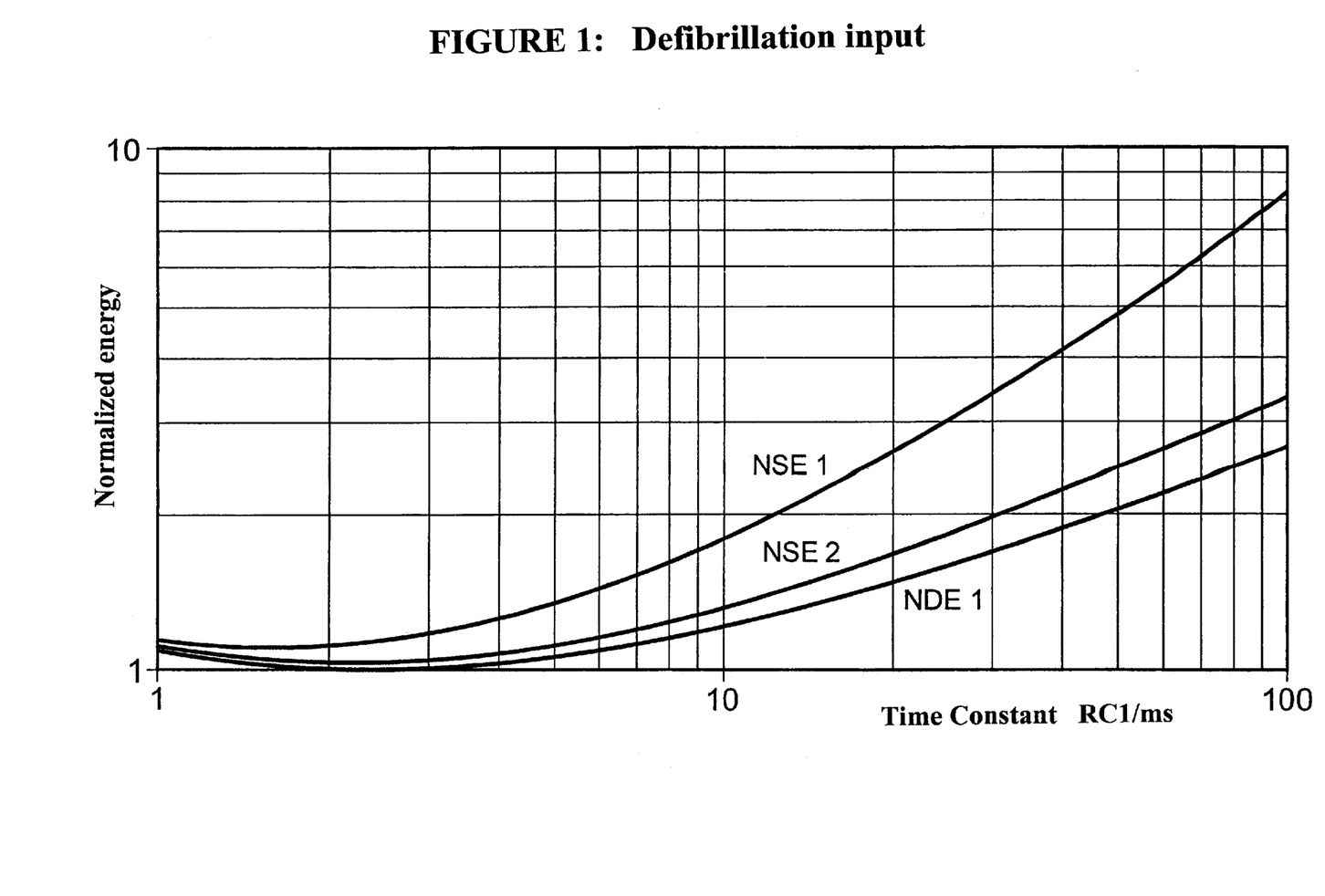
FIG. 1 is a graph showing the defibrillation input in dependence on the time constant.

The reduction in the capacitance of the two-capacitor system together with the increase in the mean voltage mean that the normalized stored energy (NSE2) of a two-capacitor system above an RC-value which governs the 50% tilt extends markedly more shallowly than the curve for the one-capacitor system (see FIG. 1). The curve for the normalized stored energy (NSE1) of the one-capacitor system corresponds to the curve which is shown as FIG. 8 in Reference 4 from the Background of the Art, but which was there given with a normalized time constant. The normalized stored energy of the two-capacitor system (NSE2) is afforded by multiplication from the reduced capacitance (2C2/C1), the mean voltage altered by voltage doubling (MV1/MV2) and the NSE1 value of the one-capacitor system curve. The former simply arises out of equation (11b) by forming the ratio of 2C2 to C1, and multiplying it by the square of the ratio of the mean values of the voltages $(MV1:MV2)^2$ and the corresponding value of NSE1 (see Table 1).

An example will illustrate this operating procedure. With a time constant RC1 of 20 ms the tilt=0.340 (see Table 1), and the normalized mean value of the voltage NMV1=0.818, which also applies in regard to parallel discharge of the two C2-capacitors. The mean value of serial discharge is 0.72 (this follows from discharge to half the value) multiplied by double the exponential final value of (1-tilt) corresponding to 0.66, that is to say 0.72·1.32=0.95. That gives an overall weighted mean value NMV2 of (5.87 ms·0.818+2.45 ms·0.95): 8.32 ms=0.857 (duration of the parallel discharge= 5.87 ms, and that of the serial discharge=2.45 ms, the overall duration=8.32 ms) which is 1.048 times higher than the mean value in the case of one-capacitor discharge. The initial voltage can be correspondingly lowered, which corresponds to a reduction in the stored energy to 0.911. With equation (11b) and by analogy with (12/13), it is possible to calculate for RC1=20 ms an energy ratio E2:E1 of 0.706, which results in an overall reduction of 0.911 0.706=0.643, or, to put that another way: the normalized stored energy of the one-capacitor system NSE1 of 2.591 is reduced in the case of the two-capacitor system to an NSE2 of 0.911 ·0.705·2.591=1.666. For comparison: with a tilt of 50% NSE1=1.46 and NSE2=1.17 (see Table 1). On the assumption that with a 50% tilt with an RC2 of 2.6 ms 10 J is required for defibrillation, the one-capacitor system with RC1 of 6.5 ms would correspondingly require 12.5 J for the same effect. A two-capacitor system with a tilt of 34% and an RC2 of 7.06 ms would rise to 14.2 J and finally the one-capacitor system with RC1 of 20 ms would rise to 22.1 J. The calculation once more demonstrates the finding that the pure energy information says nothing about the effectiveness thereof.

In comparison with the example with a time constant of 20 ms, with an RC1 of 10 ms the energy is reduced to only 0.966 $(=0.984^2)$ by virtue of the excessive increase in voltage, while as stated, with a 50% tilt, there is no longer any difference as the mean voltage value is equal for both discharges.

It follows therefrom that the new method fits in well in particular with the implementation of defibrillators with large capacitors and a correspondingly low voltage.

Investigations of three works (References 5–7) in which the tilt was experimentally researched with a very low level of energy input showed that the energy with optimized tilt can actually be reduced to about 70% in comparison with a tilt of 80% (in one experiment of 88%). If consideration is further given to the reduction due to the two-capacitor system of for example 80% for a 50% tilt, then the highest mark of 30 J which was earlier established is reduced by the described two-capacitor systems to 0.8·0.7·30 J=17 J with the same effectiveness. The maximum energy required would therefore fall still further if the capacitors were selected to be still smaller than the above-calculated 52 $\mu$F with a tilt of 50%, which however involves increased voltages. Thus for example a capacitor of 104 $\mu$F (2·52 $\mu$F) requires just on 570 V in order to be charged up to the 17 J corresponding to the 30 J at an 80% tilt value.

Therefore Table 1 with the parameters NSE1 and NSE2 represents the required input in order to be able to effect defibrillation with the predetermined parameter (this is generally the capacitor) in comparison with the theoretically lowest delivered energy NDE with an RC1 of 2.36 ms (in an 8-digit calculation that value is to be unambiguously defined). The input for NSE1 or NSE2 which can be read off as a function of the time constant RC1 could also be interpreted as a reciprocal value which then can be interpreted as efficiency η in relation to the theoretical optimum. A horizontal line in graph 1, that is to say a predetermined level of efficiency, demonstrates the possibility in relation to larger capacitors for the two-capacitor system or conversely it also shows that under some circumstances a one-capacitor system with an RC1 of 9 ms can be more worthwhile than a two-capacitor system beyond an RC1 of 20 ms. A vertical line clearly shows the lower degree of input (or higher efficiency) if the two-capacitor system were embodied instead of the one-capacitor system. The time constant RC2 associated with the vertical line RC1 can be read off in Table 1.

The depicted two-capacitor system always reduces its residual voltage U2(residue) to half the value of the corresponding one-capacitor system U1(residue). That means however that the new system can only supply half the voltage for a bi-phase pulse. In accordance with the current school of thought this is deemed to be detrimental as the second phase is attributed with a crucial action which in our view it does not enjoy. Nonetheless discharge of the residual voltage of the two-capacitor system is advantageous, preferably if that again happens in parallel. That would counteract in particular "over-stimulation in the proximity of the cardiac electrode" (Reference 4).

It is possible to see from FIG. 1:
how the delivered energy NDE1 of the one-capacitor system increases as a reference value with an increasing time constant (lower curve),
how the stored energy NSE1 of the one-capacitor system increases over-proportionally with the time constant (upper curve),
how the stored energy of the two-capacitor system NSE2 (curve in the middle) remains markedly below that of the one-capacitor system NSE1, particularly when large time constants are involved, and how far away we are from the theoretical minimum NDE1 at RC1=2.36 ms.

While NSE1 or NSE2 represent the input which must be provided in relation to the theoretical minimum with a one-capacitor system or a two-capacitor system, the reciprocal $\eta_1 = 1/\text{NSE1}$ and $\eta_2 = 1/\text{NSE2}$ corresponds to the efficiency in which both electrical and also physiological optimization is expressed and which relates to the theoretical minimum of the delivered energy NDE1 with an RC1 of 2.36 ms.

Figure 2:
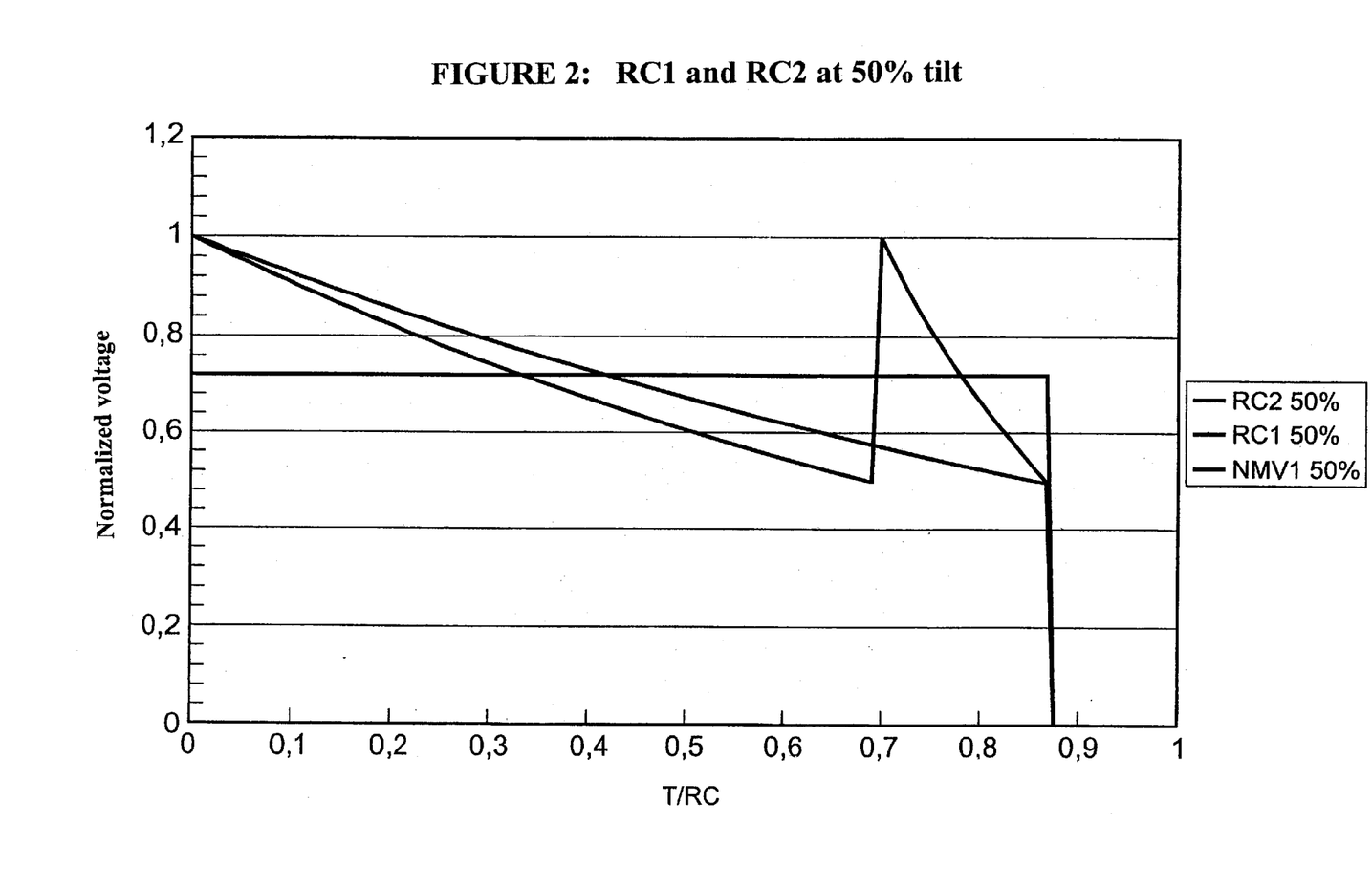
FIG. 2 is a graph showing RC1 and RC2 at 50% tilt.

FIG. 2 is a representation of the discharge calculated with equation (12) at 50% tilt for RC1 and RC2. The RC1 curve ends at T/RC=0.9 (in reality at 4.5 ms) at a normalized voltage of 0.5, while the exponential curvature can scarcely be perceived. That is also expressed in the mean normalized voltage NMV1 which at 0.721 is only slightly lower than the linear mean value at 0.75. "Mean value" means that the wedge part of the discharge curve above the mean value line is equal in terms of surface area to that beneath the discharge curve. More specifically, in the total of three discharge curves with RC1, 2·RC2 and ½·RC2 it will be apparent, which has been theoretically worked out with formula (7), that the mean value of the voltage depends only on the tilt and not on the time constant. In all three discharges the wedge compensation effect is very beautifully demonstrated by the one line at 0.721. That affords the same normalized voltage for both discharge curves and thus the same physiological effectiveness.

Figure 3:
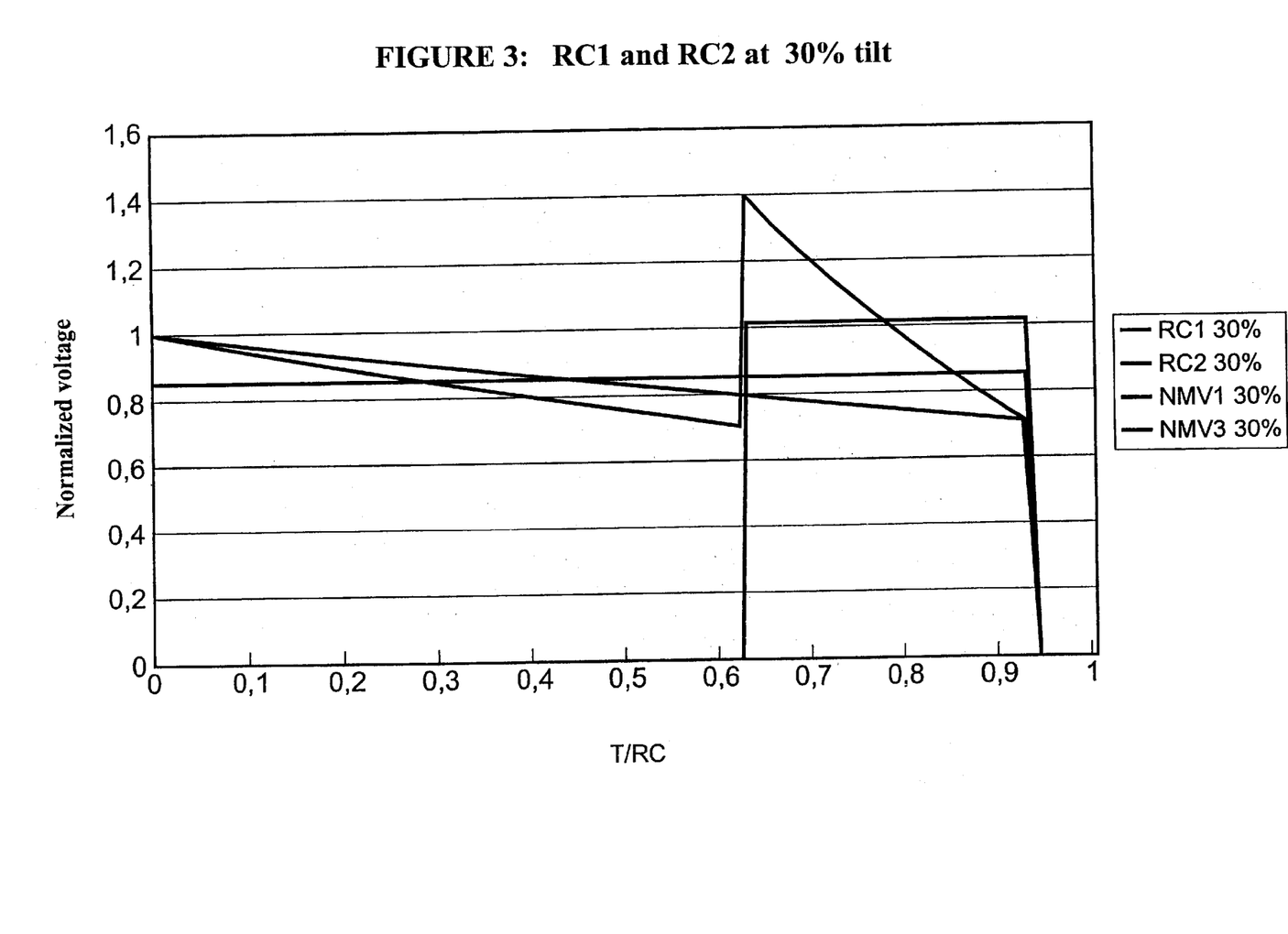
FIG. 3 is a graph showing RC1 and RC2 at 30% tilt.

FIG. 3 predetermines an RC1 discharge at 70% (tilt then 30%, RC1=27.5 ms). The curve ends at an T/RC of 0.94 (in actual fact at 9.8 ms). At 0.625 (6.6 ms in reality) the discharge is terminated with 2·RC2 and voltage doubling to the normalized value of 1.4 begins. After 2.8 ms the discharge procedure with ½·RC1 has then occurred again at 0.7, and the line NMV3 indicates the mean value which is 0.165 higher than that of the RC1 curve. As a result the discharge with RC2 and subsequent voltage doubling is physiologically more effective with the same initial voltage (here 1). The effectiveness becomes the same if the initial voltage of the RC2 curve is reduced to 94% in relation to the RC1 curve. In energy terms that denotes a reduction to 88%. In this example however the efficiency $\eta_2$ at 0.53 (see Table 1) is already very low, which again is already reached by an RC1 discharge at approximately an RC1 of 11.5 ms (corresponding to a tilt of 41%).

It is not only possible to deduce that for each time constant RC1 there is an individual optimum tilt, but also how great the chronaxie time is, which in the calculation forms the important value for normalization of the system of equations. With knowledge of the optimum tilt and the corresponding time constant it is possible to ascertain from Table A of [4], at which tilt which normalized time constant V=RC/chronaxie occurs. The chronaxie in relation to defibrillation of implanted units is to be fixed approximately at:

$$t_{chronaxie} = 2 \text{ ms} \tag{16}$$

Estimates show that this value may individually alter by ±30%, which however has a less than 20% effect on the results or upon optimization. If there should be a chronaxie which is markedly different from 2 ms, for example due to other electrodes or other defibrillation modes, it is nonetheless possible to use the results in Table 1, it is only necessary to multiply all time values by the factor c:

$$C = t_{chronaxie}/2 \text{ ms} \tag{17}$$

The time constant RC1 in the first column arises out of multiplication of the value V in Table A from Reference 4 with the chronaxie in accordance with equation (16) of 2 ms.

The pulse duration T1 in the second column is obtained like RC1 from the value X in Table A and chronaxie.

The tilt was created in such a way that the first two columns in Table A of Ref. 4 were over-written with the new values for RC1 and T1.

NMV1 is the mean value of the voltage as a function of RC1 and during the pulse duration T1. A calculation formula was already afforded with equation (3). In deriving that formula the expression T1/RC1 which occurs upon integration was replaced by the expression In[U(o):U(residue)]. The normalized mean voltage NMV1 in accordance with equation (7) is thereby dependent only on the tilt.

The normalized delivered energy NDE1 (related to the minimum at RC1=2.36 ms) was obtained like tilt from Table A of Reference 4. The efficiency Eta from that Table A was electrically defined as the ratio of delivered energy (NDE) to stored energy (NSE).

The mode of operation of the method according to the invention is to be set forth in summarizing form once again hereinafter as follows:

The normalized stored energy NSE1 is defined by the quotient NDE1 divided by Eta. RC2 is determined in accordance with equation (11a).

T(2) (time during the discharge of RC2) is calculated from the combination of equations (5) and (8):

$$T(2) = RC2 \text{In}(1\text{-tilt}) \tag{18}$$

T(3) (time during the discharge of the series circuit to half the voltage value) is determined in analogous fashion:

$$T(3) = 0.5 RC2 \text{In} 2 \tag{19}$$

NMV(2) is the mean voltage during the time T(2) corresponding to equation (7).

NMV(3) is the mean voltage during T(3) which with the equations (5) and (7) having regard to discharge to half the value is calculated as follows:

$$NMV(3) = 2 \cdot (1 - \text{tilt}) \cdot (0.5 : \text{In} 2) = 1.4427 \cdot (1 - \text{tilt}) \tag{20}$$

NMV2 is the voltage averaged over the times T(2) and T(3):

$$NMV2 = [2 \cdot NMV(2) \cdot T(2) + NMV(3) \cdot T(3)] : T1 \tag{21}$$

MV1:MV2 is the quotient which characterizes the increase (or reduction) in voltage on the basis of the parallel-series circuit configuration.

2C2:C1 indicates the reduction in the stored energy in the case of the two-capacitor system in comparison with the one-capacitor system.

NSE2 is the normalized stored energy which arises out of:

$$NSE2 = NSE1 \cdot (2C2:C1) \cdot (MV1:MV2)^2 \tag{22}$$

The reciprocal value of NSE2 represents the efficiency $\eta_2$ which is related to the energy minimum NDE1 at RC1=2.36 ms.

NSE2:NSE1 is identical to the ratio of the efficiencies $\eta_1 : \eta_2$ and demonstrates the superiority of the two-capacitor system in particular in relation to a high RC1. (In the same manner, as indicated previously, it is also possible to calculate systems with more than two capacitors).

Accordingly the combination of theoretically well-founded pulse duration or tilt with the principle of voltage doubling by means of two capacitors affords a technical advance which can be used in various ways. Measurement of the time constant during parallel or sequential discharge can thus be advantageously used to ascertain the corresponding tilt and to cause the pulse to cease when it is reached. That applies both in regard to the individual capacitors and also in regard to the serial connection thereof. It is thus best possible to do justice to any situation with an unknown defibrillation impedance.

All calculations were based on the assumption that the chronaxie in the defibrillation procedure is 2 ms. If that value should be found to be incorrect, for example fluctuating by up to 30%, the method of the invention would not be rendered ineffective as a result as as a consequence the tilt changes by less than 16%. That affords the advantageous development of making the tilt which is so important in terms of the effectiveness of the method variable by up to 20% by programming.

The curve NSE2 in FIG. 1 demonstrates the input which is to be achieved with the two-capacitor system and which cannot be surpassed by any system known at the present day. The reciprocal of that value (NSE2$^{-1}$) defines the efficiency $\eta_2$ which gives the defibrillator its name. This therefore means not one defibrillator but a family which is dimensioned in accordance with the equations (11) for the two-capacitor system and which is optimized in the inverse relationship to the equation (22):

$$\eta_2 = \text{NSE2}^{-1} = \text{NSE1}^{-1} \cdot \{C1/2C2\} \cdot \{NMV2/NMV1\}^2 \qquad (25)$$

wherein:

NSE2=normalized stored energy of the two-capacitor system,

NSE1=normalized stored energy of the one-capacitor system,

C1/2C2=ratio of the capacitances of the one—and two-capacitor systems respectively, NMV2=normalized mean voltage of the two-capacitor system, and NMV1=normalized mean voltage of the one-capacitor system.

All values are set out in Table 1 as a function of the time constant RC1 for the range between 1.0 ms and 100 ms. For the corner points of a realistic range of between 2.5 ms and 20 ms the ETA values read as follows:

$\eta_2$(2.5 ms)=0.969 (3% more energy necessary in comparison with the reference value NDE1 (2.36 ms)), and $\eta_2$(20 ms)=0.60, thus $\eta_2$ is higher by the factor of 1.56 than $\eta_1$(20 ms)=0.386 (=1:2.592)

The reduction in input as shown in FIG. 1 by virtue of two capacitors or the increase in efficiency (as a reciprocal value of input) $\eta_2$ is to be attributed exclusively to optimization of the pulse which in the case of a "bi-phase" pulse would correspond to the first phase. There is nothing against also discharging the residual voltage of the two-capacitor system as a second inverted phase, in which case that should preferably take place in the form of a parallel discharge.

Figure 4:
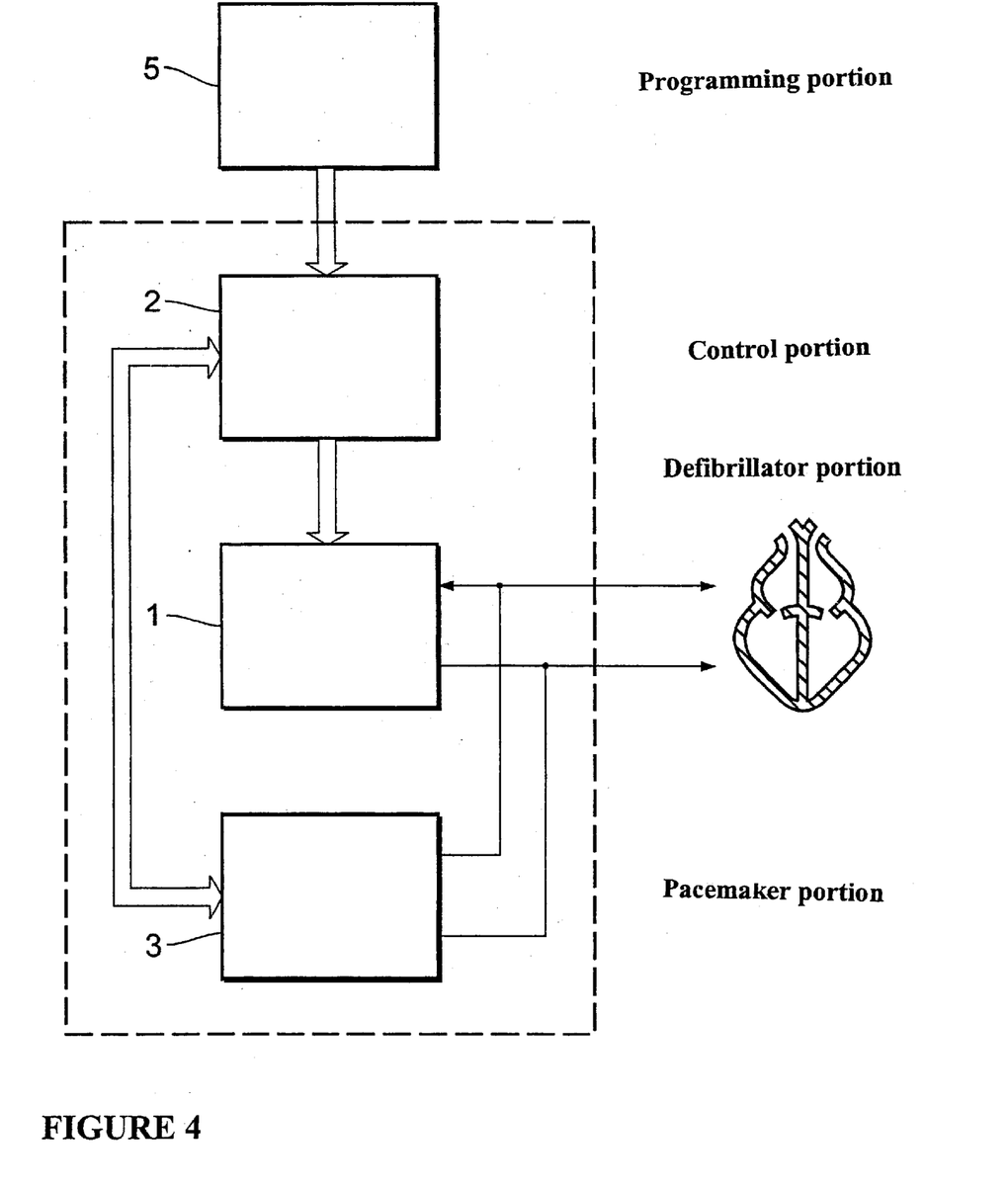
FIG. 4 shows a block circuit diagram of the basic components of an embodiment of the defibrillator according to the invention.

Referring to FIG. 4, an advantageous structural embodiment of the invention in the form of an implantable cardioverter defibrillator (ICD) is shown in the form of a block circuit diagram. For operation thereof this embodiment thus also makes use of the method according to the invention. The block circuit diagram shows the co-operation in principle of the groups shown in the following Figures. A defibrillator portion 1 produces the pulses which are to be delivered to the heart in a defibrillation phase and includes the energy source required for that purpose. The defibrillator portion 1 is connected to a control portion 2 containing the groups which establish the stimulation defibrillation times and determine the configuration in respect of time of the defibrillation pulses. A cardiac pacemaker portion 3 contains the usual functions of an implantable pacemaker and implements control in respect of time of the stimulation pulses which are necessary to maintain the normal cardiac activity in the bradycardia and tachycardia range. That also includes recognition of irregularities in cardiac activity from the intracardial electrocardiogram recorded by way of the implanted electrodes. The control portion 2 also has control over the pacemaker portion 3 so that in that way the functions thereof can also be remotely programmed and controlled in time-synchronized relationship with the behavior of the heart. The groups 1 through 3 are combined in a casing 4 which is represented symbolically by a broken line. The implanted portions which are disposed in the casing 4 are remotely controllable and remotely settable by a programming portion 5 from outside the body. In addition the configuration in respect of time of the cardiac events and the stimulation and defibrillation measures which are thereupon initiated is recorded in the control portion and if necessary can be transmitted by means of the programming portion to the exterior of the body and can there be evaluated by the doctor.

Figure 5:
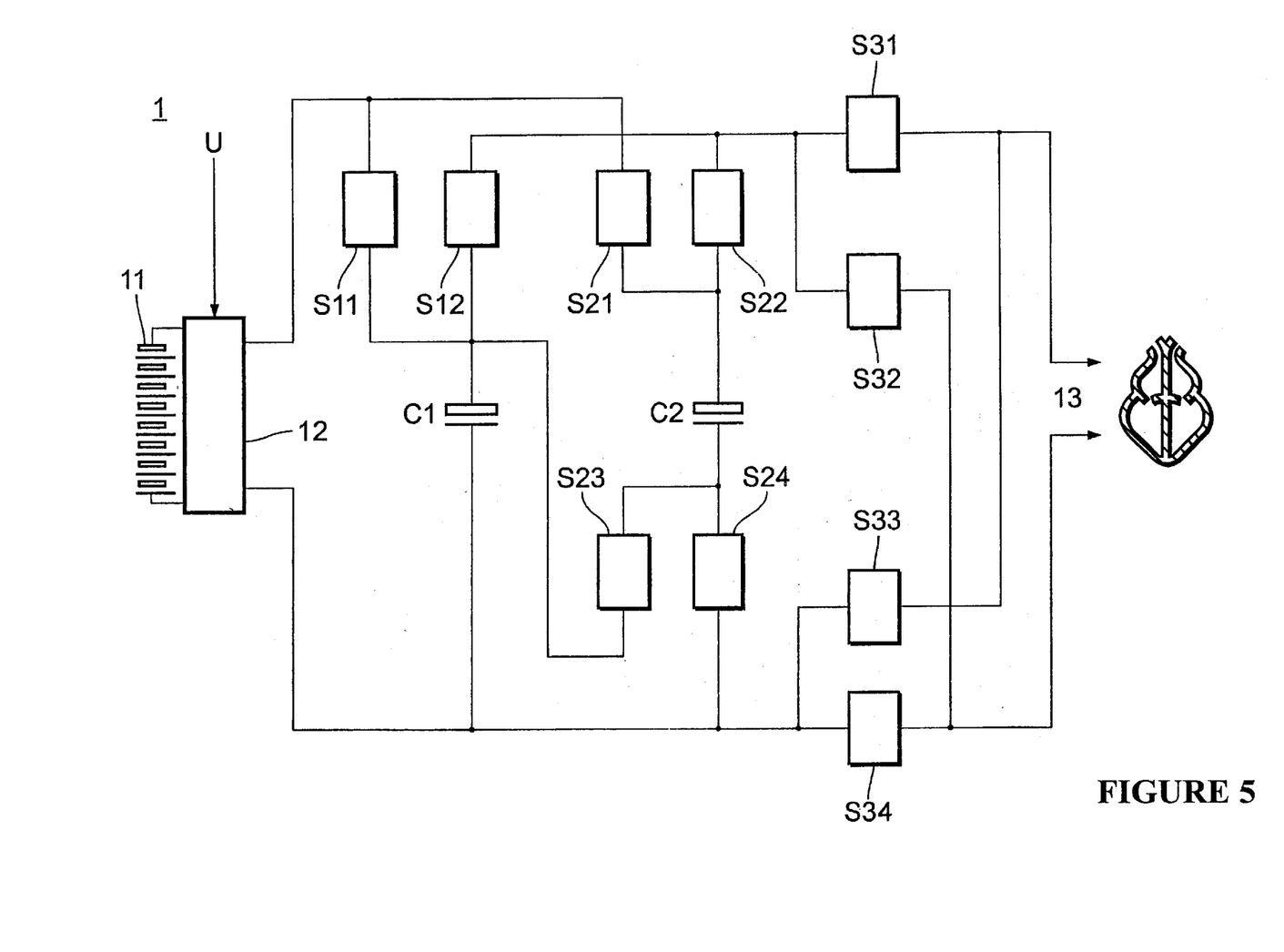
FIG. 5 shows a block circuit diagram of the defibrillator portion of the embodiment of FIG. 1.

FIG. 5 shows in detail the functional components of the defibrillator portion 1. In this case an energy source 11 which is in the form of a conventional battery serves as a power supply for this group. Connected on the output side of the energy source 11 is a voltage transformer 12 which boosts the output voltage of the battery to a settable supply voltage U for charging up the subsequent capacitors C1 and C2. The internal resistance of the voltage transformer 12 is such that charging-up of the capacitors C1 and C2 takes place in a suitably short period of time, after which in the situation requiring defibrillation it was activated by way of a suitable control line from the control portion 2. The capacitors C1 and C2 can be connected by way of various switching elements S11 through S34 in various ways to the voltage transformer 12 on the one hand and the cardiac electrode 13 on the other hand, as is described in greater detail hereinafter. In this respect, activation of one or more of the switching elements S11 through S34 means that the switching element in question in switched into the conducting condition for a predetermined period of time.

For the charging operation, the capacitors C1 and C2 are connected directly to the output of the voltage transformer 12 by activation of the switching elements S11 and S22, so that the capacitors are charged up to their set initial voltage. In that case the charging operation is effected in a suitably short period of time according to the internal resistance of the voltage transformer.

Discharge of the energy stored in the capacitors C1 and C2 to the electrode 13 which is connected to the heart is effected either sequentially in respect of time by successive activation of the switching elements S12 for C1 and S12 and S24 for C2 for two successive periods of time or by simultaneous activation of the corresponding switching elements in a single period of time.

In this case, connection to the heart by way of the electrodes 13 is effected by activation of the switching elements S31 and S32 each in a first polarity.

A further discharge configuration is afforded by a series connection of the capacitors C1 and C2 by activation of the switching elements S22 and S23. In this case once again the switching elements S31 and S33 are activated for discharge in the first polarity.

To reverse the discharge configurations for a possible residual discharge in the bi-phase mode of operation, the switching elements S32 and S34 are activated instead of the switching elements S31 and S33.

Figure 6:
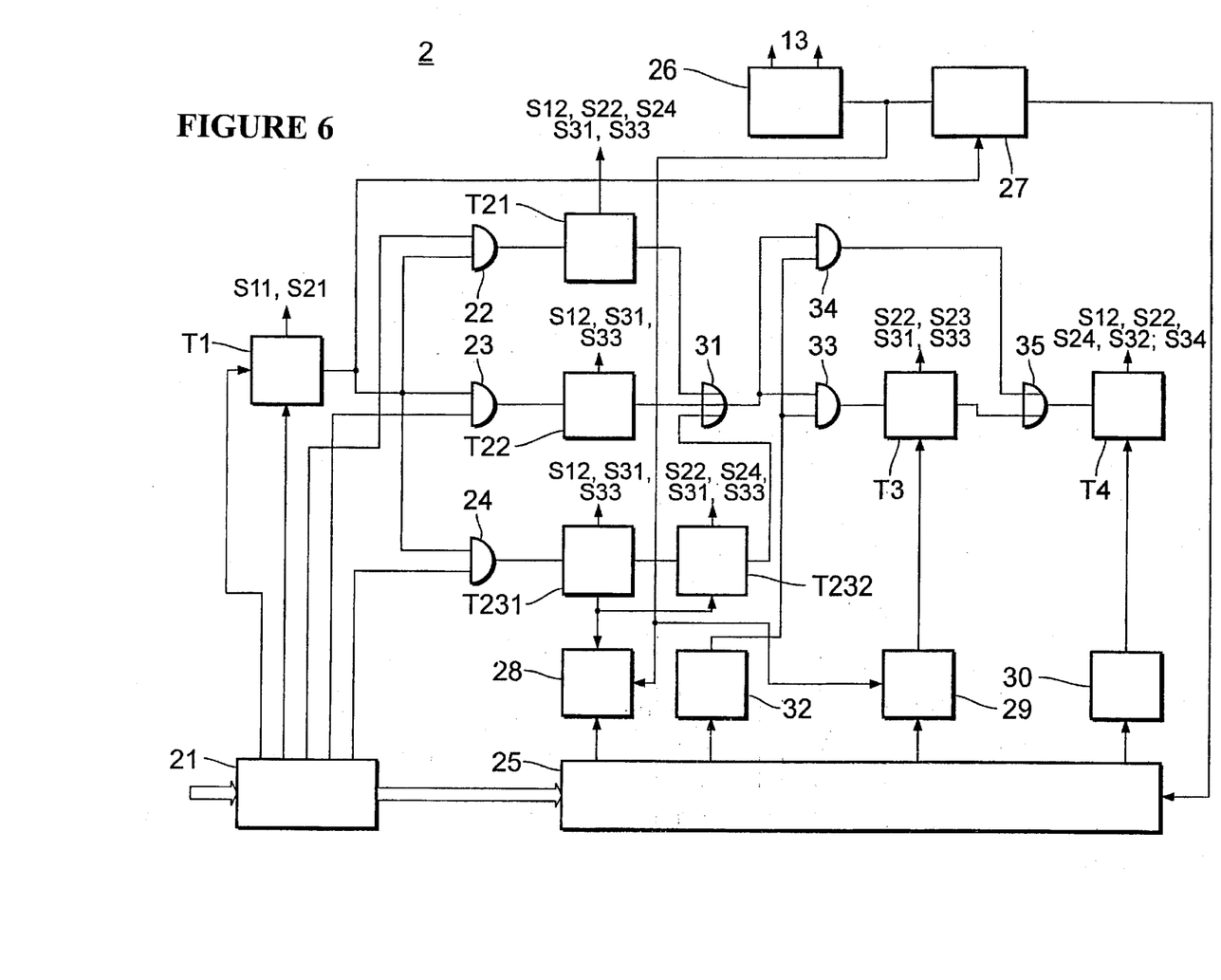
FIG. 6 shows a block circuit diagram of the control portion of the embodiment of FIG. 4.

Reference is now made to FIG. 6 to describe the production of the controls signals, with the control portion 2, which cause activation of the switching elements S11 through S34 for predetermined periods of time.

The timer blocks shown in FIG. 6 are respectively activated by a starting pulse by an input signal which is fed to the illustrated block from the left-hand side in the drawing. They respectively remain active for a predetermined period of time which is characteristic for the block and which can possibly be altered by way of external programming means (programming portion 1 in FIG. 1) and in that respect deliver a suitable control signal to the above-mentioned switching elements S11 through S34 of the defibrillator portion shown in FIG. 5. The signal connections in question leave the respective timer block upwardly in the drawing. After the expiry of the period of time which is characteristic of the respective timer block the timer blocks in question each output a control pulse which possibly serves for activation of a subsequent timer block. The corresponding signal paths leave the respective timer block towards the right in the drawing.

When defibrillation is necessary, the timer block T1 which determines the charging times of the capacitors C1 and C23 by means of control signals and the switching elements S11 and S22 is supplied with a suitable starting signal from a time control unit 21 which holds the supremacy in terms of time control. After charging is concluded that procedure is terminated by a suitable end signal to the timer block T1. The time duration of the charging procedure can possibly be set from the exterior, like also the charging voltage of the voltage transformer 12 in FIG. 5.

The output signal of the timer block T1 is fed to three AND-gates 22 through 24, to the further input of each of which passes a respective one of three control signals of the time control unit 21, which select which of three subsequently connected timer blocks T21, T22 or T231 is activated by the output signal of the timer block T1. In this respect, the choice of the respective timer block determines which of three first discharge configurations is selected for the capacitors C1 and C2. These are parallel discharge (T21), individual discharge (T22) and sequential discharge (T231 and T232). In that way it is possible by means of the time control unit by virtue of external programming to establish which of the three first discharge configurations is adopted. In the case of the parallel discharge configuration being selected, the switching elements S12, S22, S24, S31 and S33 are activated by the time control unit T21. In contrast, in the case of the individual capacitor discharge configuration being selected, the switching elements S12, S31 and S33 are activated by the time control unit T22 and, in the case of selection of the sequential discharge configuration, the switching elements S12, S31 and S33 are activated firstly—as in the above-mentioned case—by the time control unit T231.

The control signals for termination of the signal output for the various timer blocks are produced by a control unit for discharge termination as indicated at 25. That control unit determines the end of discharge of the capacitors C1 and C2 to provide for optimization in accordance with the invention of the discharge energy from the time constant arising in regard to discharge and the remaining residual discharge voltage which is ascertained in dependence thereon. Ascertaining the discharge voltage in that way can be effected either by using a look-up table in the manner of Table 1 in such a way that, after the time constant RC1 has been ascertained the corresponding tilt value (or that of the corresponding residual voltage) is outputted, or that value is calculated on the basis of the specified relationships.

To ascertain the appropriate operating parameters which are also used as an input parameter for the group 26, the arrangement has a volt meter 26 which ascertains the current voltage at the electrodes 13. The configuration of the voltage at the beginning of the discharge is taken—derived from the corresponding starting signal as the output signal of the time control block T1—with the beginning of the first phase of discharge of the capacitors C1 and C2 respectively, by means of a suitable group, to determine the time constant of the discharge procedure, which forms the product of the respective discharge capacitance and the resistance of the electrode 13. The discharge voltage at which discharge is terminated depends on that time constant. That is effected with what is known as a look-up table in which the residual voltages at which the discharge is to be terminated in the respective phase are recorded in dependence on the ascertained time constant. That table is shown in greater detail as Table 1. When the voltage which is ascertained for the respective discharge configuration on the basis of the ascertained time constant is reached, a signal is delivered to the time control block which controls the discharge, that signal terminating the corresponding discharge time and possibly starting the next discharge phase by the appropriate control signal which indicates termination of the period of time in question. That is effected by activation of the subsequent time control block.

In the case of sequential discharge, after discharge of the first capacitor C1 to the ascertained discharge voltage, the second capacitor is discharged (to the same discharge voltage). For that purpose, the block T232 is activated by the output signal of the block T231 and activates the switching elements S22, S24, S31 and S33. Termination of that discharge phase again occurs when the predetermined discharge voltage is reached. In a corresponding fashion, a timer pulse starting a subsequent time control block is also supplied by the block T232. That is effected by the discharge voltage associated with the respectively ascertained time constant being ascertained from the control unit for the end of discharge as indicated at 25, and being fed to the voltage comparator 28 through 30 associated with the respective discharge phase (active time control block). As soon as the current discharge voltage which is ascertained by the volt meter 26 reaches or falls below the value held in the respective voltage comparator, it delivers the control signal for terminating discharge in the respective phase.

The output pulses of the time control blocks T21, T22 and T232 are combined together by way of an OR-gate 31. The output signal of that OR-gate 31 serves for actuation of the subsequent time control blocks. In the normal case this is the time control block T3 which triggers serial discharge of the two capacitors C1 and C2 by activation of the switching blocks S22, S23, S31 and S33. That serial discharge can possibly also be omitted under certain circumstances. This is also established by the time constants determined with the group 27.

A selection block 32 determines the further discharge sequence by means of two AND-gates 32 and 33. In dependence on the output signal of the selection block which in turn is actuated by the control unit 25 for terminating discharge, the output signal of the OR-gate 31 is passed either by way of the AND-gate 33 to the time control block T3 or by way of the AND-gate 34 and a further OR-gate 35 to the time control block T4. In the case of activation of the time control block T3 the above-described serial discharge takes place while in the other situation parallel bi-phase residual discharge similarly takes by way of the time control block T4. In this respect the residual charge of the capacitors C1 and C2 is discharged after attainment of the respective end of the discharge procedure, at the threshold voltages in question, with a bi-phase voltage reversal. In this respect, the arrangement ascertains by way of the voltage comparator 30 when the output voltage at the electrodes has reached a residual voltage. That residual voltage is fixedly stored in the voltage comparator.

In the other situation, more specifically when series discharge is skipped, activation of the time control block T4 for activating bi-phase discharge is effected by way of the AND-gate 34 on the basis of the corresponding output signal of the selection circuit 32 immediately after activation of one of the time control blocks T21, T22 or T232.

Instead of the normalized residual voltage or the tilt, "shut-down" of the respective capacitor combination at the intended residual voltage can also be effected by means of a suitable time presetting which is respectively established starting from the initial voltage, on the basis of the ascertained time constant. The time control blocks shown in FIG. 3 are then not each reset by an external control signal which marks the end of the respective period of time, but receive the remaining residual time ascertained as set forth hereinbefore, transmitted from the unit 25. Then, after expiry of the residual time, this being controlled by suitable timer means, delivery of the signal identifying the end of the respective period of time takes place for evaluation of the further control procedures towards the right in the drawing, as was described hereinbefore.

The invention is not limited to the illustrated embodiments and in particular it is not bound to a configuration in just hardware or just software terms as the primary consideration is the described functionality, more specifically the described behavior of the system as a reaction to the input conditions set forth. In this respect the structure of timing members used can also serve as a starting point for the design of a suitable flowchart as a basis for control software, in which respect the procedures which are reproduced in parallelized mode only have to be edited in the manner of a flowchart with the corresponding logical links for serial processing. It therefore also immaterial whether the system is used as an implantable or external system or also as part of a larger overall system. Thus the described functionality can also serve for example as an operating procedure for a system of higher order, and in particular in regard to ascertaining the respective operating parameters it is possible to make use with the same degree of success both of the respectively specified calculation methods and also look-up tables in which the stored values are each looked up and read off.

TABLE 1

| RC1/ms | T1/ms | Tilt | NMV1 | NDE1 | Eta | NSE1 | RC2 | T(2) | T(3) | NMV(2) | NMV(3) | NMV2 | MV1:MV2 | 2C2:C1 | NSE2 | ETA2 | SE2:SE1 |
|---|---|---|---|---|---|---|---|---|---|---|---|---|---|---|---|---|---|
| 1.00 | 1.51 | 0.7780 | 0.5169 | 1.0876 | 0.9507 | 1.1440 | 0.4484 | 0.6749 | 0.1554 | 0.5169 | 0.3202 | 0.4966 | 1.0409 | 0.8968 | 1.1115 | 0.8997 | 0.9716 |
| 1.10 | 1.60 | 0.7658 | 0.5276 | 1.0683 | 0.9451 | 1.1303 | 0.4913 | 0.7132 | 0.1703 | 0.5276 | 0.3379 | 0.5073 | 1.0399 | 0.8934 | 1.0919 | 0.9159 | 0.9660 |
| 1.20 | 1.68 | 0.7543 | 0.5374 | 1.0530 | 0.9396 | 1.1206 | 0.5341 | 0.7497 | 0.1851 | 0.5374 | 0.3544 | 0.5173 | 1.0389 | 0.8901 | 1.0765 | 0.9289 | 0.9606 |
| 1.30 | 1.77 | 0.7435 | 0.5464 | 1.0408 | 0.9342 | 1.1140 | 0.5766 | 0.7846 | 0.1998 | 0.5464 | 0.3700 | 0.5265 | 1.0379 | 0.8870 | 1.0644 | 0.9395 | 0.9555 |
| 1.40 | 1.85 | 0.7334 | 0.5548 | 1.0310 | 0.9289 | 1.1099 | 2.7821 | 0.8181 | 0.2145 | 0.5548 | 0.3847 | 0.5351 | 1.0368 | 0.8841 | 1.0549 | 0.9479 | 0.9505 |
| 1.50 | 1.93 | 0.7237 | 0.5626 | 1.0232 | 0.9237 | 1.1077 | 0.6610 | 0.8503 | 0.2291 | 0.5626 | 0.3986 | 0.5431 | 1.0359 | 0.8813 | 1.0475 | 0.9547 | 0.9456 |
| 1.60 | 2.01 | 0.7146 | 0.5699 | 1.0170 | 0.9185 | 1.1072 | 0.7029 | 0.8813 | 0.2436 | 0.5699 | 0.4117 | 0.5507 | 1.0349 | 0.8786 | 1.0418 | 0.9599 | 0.9409 |
| 1.70 | 2.08 | 0.7059 | 0.5768 | 1.0121 | 0.9135 | 1.1079 | 0.7446 | 0.9113 | 0.2581 | 0.5768 | 0.4243 | 0.5579 | 1.0339 | 0.8760 | 1.0374 | 0.9640 | 0.9364 |
| 1.80 | 2.15 | 0.6976 | 0.5833 | 1.0082 | 0.9086 | 1.1097 | 0.7861 | 0.9403 | 0.2724 | 0.5833 | 0.4362 | 0.5646 | 1.0329 | 0.8735 | 1.0342 | 0.9670 | 0.9320 |
| 1.90 | 2.22 | 0.6897 | 0.5894 | 1.0053 | 0.9037 | 1.1124 | 0.8275 | 0.9684 | 0.2868 | 0.5894 | 0.4476 | 0.5711 | 1.0320 | 0.8710 | 1.0319 | 0.9691 | 0.9277 |
| 2.00 | 2.29 | 0.6822 | 0.5951 | 1.0031 | 0.8990 | 1.1158 | 0.8687 | 0.9957 | 0.3011 | 0.5951 | 0.4586 | 0.5772 | 1.0311 | 0.8687 | 1.0305 | 0.9704 | 0.9235 |
| 2.10 | 2.36 | 0.6749 | 0.6006 | 1.0016 | 0.8943 | 1.1199 | 0.9097 | 1.0222 | 0.3153 | 0.6006 | 0.4690 | 0.5831 | 1.0302 | 0.8664 | 1.0297 | 0.9711 | 0.9194 |
| 2.20 | 2.43 | 0.6679 | 0.6059 | 1.0006 | 0.8897 | 1.1246 | 0.9506 | 1.0480 | 0.3294 | 0.6059 | 0.4791 | 0.5886 | 1.0293 | 0.8642 | 1.0295 | 0.9713 | 0.9155 |
| 2.30 | 2.49 | 0.6613 | 0.6109 | 1.0001 | 0.8853 | 1.1297 | 0.9913 | 1.0731 | 0.3436 | 0.6109 | 0.4887 | 0.5940 | 1.0284 | 0.8620 | 1.0299 | 0.9710 | 0.9116 |
| 2.40 | 2.55 | 0.6548 | 0.6156 | 1.0000 | 0.8808 | 1.1353 | 1.0319 | 1.0976 | 0.3576 | 0.6156 | 0.4980 | 0.5991 | 1.0275 | 0.8599 | 1.0307 | 0.9702 | 0.9079 |
| 2.50 | 2.61 | 0.6486 | 0.6202 | 1.0003 | 0.8765 | 1.1412 | 1.0723 | 1.1215 | 0.3716 | 0.6202 | 0.5069 | 0.6041 | 1.0266 | 0.8579 | 1.0319 | 0.9691 | 0.9042 |
| 2.60 | 2.68 | 0.6426 | 0.6245 | 1.0009 | 0.8723 | 1.1474 | 1.1126 | 1.1449 | 0.3856 | 0.6245 | 0.5156 | 0.6088 | 1.0258 | 0.8559 | 1.0334 | 0.9677 | 0.9006 |
| 2.80 | 2.79 | 0.6313 | 0.6327 | 1.0029 | 0.8640 | 1.1607 | 1.1928 | 1.1900 | 0.4134 | 0.6327 | 0.5320 | 0.6178 | 1.0241 | 0.8520 | 1.0372 | 0.9641 | 0.8936 |
| 3.00 | 2.91 | 0.6206 | 0.6403 | 1.0057 | 0.8561 | 1.1748 | 1.2725 | 1.2333 | 0.4410 | 0.6403 | 0.5473 | 0.6262 | 1.0225 | 0.8483 | 1.0420 | 0.9597 | 0.8870 |
| 3.20 | 3.02 | 0.6106 | 0.6474 | 1.0092 | 0.8484 | 1.1896 | 1.3517 | 1.2749 | 0.4685 | 0.6474 | 0.5618 | 0.6341 | 1.0210 | 0.8448 | 1.0475 | 0.9546 | 0.8806 |
| 3.40 | 3.13 | 0.6012 | 0.6540 | 1.0133 | 0.8410 | 1.2049 | 1.4304 | 1.3149 | 0.4957 | 0.6540 | 0.5753 | 0.6415 | 1.0194 | 0.8414 | 1.0536 | 0.9491 | 0.8744 |
| 3.60 | 3.23 | 0.5923 | 0.6601 | 1.0178 | 0.8338 | 1.2207 | 1.5086 | 1.3536 | 0.5229 | 0.6601 | 0.5882 | 0.6485 | 1.0180 | 0.8381 | 1.0602 | 0.9432 | 0.8685 |
| 3.60 | 3.33 | 0.5839 | 0.6659 | 1.0226 | 0.8268 | 1.2368 | 1.5864 | 1.3909 | 0.5498 | 0.6659 | 0.6004 | 0.6551 | 1.0165 | 0.8350 | 1.0671 | 0.9371 | 0.8628 |
| 3.80 | 3.43 | 0.5759 | 0.6714 | 1.0278 | 0.8201 | 1.2532 | 1.6638 | 1.4270 | 0.5766 | 0.6714 | 0.6119 | 0.6614 | 1.0151 | 0.8319 | 1.0743 | 0.9308 | 0.8573 |
| 4.00 | 3.53 | 0.5682 | 0.6766 | 1.0331 | 0.8136 | 1.2698 | 1.7408 | 1.4621 | 0.6033 | 0.6766 | 0.6229 | 0.6674 | 1.0138 | 0.8290 | 1.0818 | 0.9244 | 0.8519 |
| 4.20 | 3.62 | 0.5610 | 0.6815 | 1.0386 | 0.8072 | 1.2866 | 1.8174 | 1.4961 | 0.6299 | 0.6815 | 0.6334 | 0.6731 | 1.0124 | 0.8261 | 1.0894 | 0.9179 | 0.8467 |
| 4.40 | 3.71 | 0.5540 | 0.6861 | 1.0443 | 0.8011 | 1.3036 | 1.8936 | 1.5291 | 0.6563 | 0.6861 | 0.6434 | 0.6786 | 1.0111 | 0.8233 | 1.0972 | 0.9114 | 0.8417 |
| 4.60 | 3.81 | 0.5474 | 0.6905 | 1.0501 | 0.7951 | 1.3206 | 1.9695 | 1.5612 | 0.6826 | 0.6905 | 0.6530 | 0.6838 | 1.0098 | 0.8206 | 1.1052 | 0.9048 | 0.8369 |
| 4.80 | 3.89 | 0.5410 | 0.6947 | 1.0559 | 0.7893 | 1.3378 | 2.0450 | 1.5925 | 0.7087 | 0.6947 | 0.6622 | 0.6888 | 1.0086 | 0.8180 | 1.1132 | 0.8983 | 0.8321 |
| 5.00 | 3.89 | 0.5410 | 0.6947 | 1.0559 | 0.7893 | 1.3378 | 2.0450 | 1.5925 | 0.7087 | 0.6947 | 0.6622 | 0.6888 | 1.0086 | 0.8180 | 1.1132 | 0.8983 | 0.8321 |
| 5.40 | 4.07 | 0.5291 | 0.7026 | 1.0679 | 0.7782 | 1.3723 | 2.1949 | 1.6528 | 0.7607 | 0.7026 | 0.6794 | 0.6983 | 1.0062 | 0.8129 | 1.1294 | 0.8854 | 0.8230 |
| 5.80 | 4.23 | 0.5180 | 0.7098 | 1.0801 | 0.7677 | 1.4070 | 2.3435 | 1.7102 | 0.8122 | 0.7098 | 0.6954 | 0.7070 | 1.0039 | 0.8081 | 1.1459 | 0.8727 | 0.8144 |
| 6.20 | 4.39 | 0.5077 | 0.7164 | 1.0923 | 0.7576 | 1.4418 | 2.4909 | 1.7651 | 0.8633 | 0.7164 | 0.7103 | 0.7152 | 1.0017 | 0.8035 | 1.1624 | 0.8603 | 0.8062 |
| 6.60 | 4.55 | 0.4981 | 0.7226 | 1.1046 | 0.7481 | 1.4766 | 2.6371 | 1.8178 | 0.9139 | 0.7226 | 0.7241 | 0.7229 | 0.9996 | 0.7991 | 1.1790 | 0.8482 | 0.7984 |
| 7.00 | 4.70 | 0.4891 | 0.7283 | 1.1169 | 0.7390 | 1.5114 | 2.7821 | 1.8683 | 0.9642 | 0.7283 | 0.7371 | 0.7301 | 0.9975 | 0.7949 | 1.1995 | 0.8365 | 0.7910 |
| 7.40 | 4.85 | 0.4806 | 0.7336 | 1.1291 | 0.7303 | 1.5462 | 2.9260 | 1.9170 | 1.0141 | 0.7336 | 0.7493 | 0.7369 | 0.9956 | 0.7908 | 1.2119 | 0.8251 | 0.7838 |
| 7.80 | 4.99 | 0.4727 | 0.7386 | 1.1413 | 0.7219 | 1.5809 | 3.0689 | 1.9639 | 1.0636 | 0.7386 | 0.7608 | 0.7434 | 0.9937 | 0.7869 | 1.2283 | 0.8141 | 0.7769 |
| 8.20 | 5.13 | 0.4651 | 0.7433 | 1.1534 | 0.7139 | 1.6156 | 3.2108 | 2.0092 | 1.1128 | 0.7433 | 0.7716 | 0.7495 | 0.9918 | 0.7831 | 1.2446 | 0.8035 | 0.7704 |
| 8.60 | 5.27 | 0.4580 | 0.7478 | 1.1654 | 0.7063 | 1.6501 | 3.3518 | 2.0530 | 1.1616 | 0.7478 | 0.7819 | 0.7553 | 0.9900 | 0.7795 | 1.2607 | 0.7932 | 0.7640 |
| 9.00 | 5.40 | 0.4513 | 0.7519 | 1.1773 | 0.6989 | 1.6846 | 3.4918 | 2.0955 | 1.2101 | 0.7519 | 0.7917 | 0.7608 | 0.9883 | 0.7759 | 1.2768 | 0.7832 | 0.7579 |
| 9.40 | 5.53 | 0.4448 | 0.7559 | 1.1891 | 0.6918 | 1.7190 | 3.6308 | 2.1367 | 1.2584 | 0.7559 | 0.8009 | 0.7661 | 0.9866 | 0.7725 | 1.2926 | 0.7736 | 0.7520 |
| 10.00 | 5.72 | 0.4357 | 0.7615 | 1.2067 | 0.6816 | 1.7703 | 3.8378 | 2.1962 | 1.3301 | 0.7615 | 0.8140 | 0.7737 | 0.9842 | 0.7676 | 1.3162 | 0.7598 | 0.7435 |
| 11.00 | 6.03 | 0.4219 | 0.7699 | 1.2353 | 0.6658 | 1.8553 | 4.1787 | 2.2901 | 1.4482 | 0.7699 | 0.8340 | 0.7853 | 0.9804 | 0.7598 | 1.3548 | 0.7381 | 0.7302 |
| 12.00 | 6.32 | 0.4095 | 0.7774 | 1.2632 | 0.6513 | 1.9395 | 4.5148 | 2.3781 | 1.5647 | 0.7774 | 0.8519 | 0.7958 | 0.9768 | 0.7525 | 1.3925 | 0.7181 | 0.7180 |
| 13.00 | 6.60 | 0.3982 | 0.7841 | 1.2904 | 0.6378 | 2.0231 | 4.8463 | 2.4610 | 1.6796 | 0.7841 | 0.8682 | 0.8055 | 0.9734 | 0.7456 | 1.4293 | 0.6996 | 0.7065 |
| 14.00 | 6.87 | 0.3877 | 0.7902 | 1.3170 | 0.6253 | 2.1061 | 5.1736 | 2.5395 | 1.7930 | 0.7902 | 0.8832 | 0.8145 | 0.9703 | 0.7391 | 1.4694 | 0.6824 | 0.6958 |
| 15.00 | 7.13 | 0.3784 | 0.7958 | 1.3429 | 0.6137 | 2.1884 | 5.4969 | 2.6139 | 1.9051 | 0.7958 | 5.8831 | 0.8228 | 0.9673 | 0.7329 | 1.5006 | 0.6664 | 0.6857 |
| 16.00 | 7.39 | 0.3697 | 0.8010 | 1.3683 | 0.6027 | 2.2701 | 5.8164 | 2.6847 | 2.0158 | 0.8010 | 0.8967 | 0.8305 | 0.9644 | 0.7271 | 1.5350 | 0.6515 | 0.6762 |
| 17.00 | 7.63 | 0.3616 | 0.8057 | 1.3930 | 0.5925 | 2.3512 | 6.1324 | 2.7524 | 2.1253 | 0.8057 | 0.9093 | 0.8378 | 0.9617 | 0.7215 | 1.5688 | 0.6374 | 0.6672 |
| 18.00 | 7.87 | 0.3541 | 0.8101 | 1.4173 | 0.5828 | 2.4318 | 6.4449 | 2.8171 | 2.2336 | 0.8101 | 0.9210 | 0.8447 | 0.9591 | 0.7161 | 1.6018 | 0.6243 | 0.6587 |

TABLE 1-continued

| RC1/ms | T1/ms | Tilt | NMV1 | NDE1 | Eta | NSE1 | RC2 | T(2) | T(3) | NMV(2) | NMV(3) | NMV2 | MV1:MV2 | 2C2:C1 | NSE2 | ETA2 | SE2:SE1 |
|---|---|---|---|---|---|---|---|---|---|---|---|---|---|---|---|---|---|
| 19.00 | 8.10 | 0.3471 | 0.8142 | 1.4410 | 0.5737 | 2.5119 | 6.7543 | 2.8791 | 2.3408 | 0.8142 | 0.9420 | 0.8511 | 0.9566 | 0.7110 | 1.6342 | 0.6119 | 0.6506 |
| 20.00 | 8.32 | 0.3405 | 0.8180 | 1.4642 | 0.5650 | 2.5915 | 7.0605 | 2.9387 | 2.4470 | 0.8180 | 0.9515 | 0.8572 | 0.9542 | 0.7060 | 1.6660 | 0.6002 | 0.6429 |
| 22.00 | 8.76 | 0.3284 | 0.8249 | 1.5094 | 0.5490 | 2.7494 | 7.6642 | 3.0514 | 2.6562 | 0.8249 | 0.9689 | 0.8686 | 0.9497 | 0.6967 | 1.7279 | 0.5787 | 0.6285 |
| 24.00 | 9.17 | 0.3177 | 0.8311 | 1.5529 | 0.5344 | 2.9056 | 8.2569 | 3.1563 | 2.8616 | 0.8311 | 0.9844 | 0.8789 | 0.9456 | 0.6881 | 1.7876 | 0.5594 | 0.6152 |
| 25.00 | 9.38 | 0.3127 | 0.8339 | 1.5740 | 0.5277 | 2.9831 | 8.5495 | 3.2062 | 2.9630 | 0.8339 | 0.9915 | 0.8837 | 0.9436 | 0.6840 | 1.8168 | 0.5504 | 0.6090 |
| 30.00 | 10.33 | 0.2912 | 0.8461 | 1.6750 | 0.4976 | 3.3659 | 9.9772 | 3.4343 | 3.4578 | 0.8461 | 1.0225 | 0.9052 | 0.9347 | 0.6651 | 1.9560 | 0.5113 | 0.5811 |
| 35.00 | 11.20 | 0.2739 | 0.8558 | 1.7688 | 0.4728 | 3.7415 | 11.3529 | 3.6334 | 3.9346 | 0.8558 | 1.0476 | 0.9231 | 0.9270 | 0.6487 | 2.0859 | 0.4794 | 0.5575 |
| 40.00 | 12.02 | 0.2595 | 0.8638 | 1.8568 | 0.4516 | 4.1113 | 12.6835 | 3.8102 | 4.3958 | 0.8638 | 1.0683 | 0.9386 | 0.9203 | 0.6342 | 2.2081 | 0.4529 | 0.5371 |
| 45.00 | 12.78 | 0.2473 | 0.8705 | 1.9399 | 0.4334 | 4.4763 | 13.9744 | 3.9692 | 4.8431 | 0.8705 | 1.0860 | 0.9522 | 0.9143 | 0.6211 | 2.3238 | 0.4303 | 0.5191 |
| 50.00 | 13.51 | 0.2367 | 0.8763 | 2.0189 | 0.4174 | 4.8371 | 15.2297 | 4.1138 | 5.2782 | 0.8763 | 1.1012 | 0.9642 | 0.9089 | 0.6092 | 2.4340 | 0.4108 | 0.5032 |
| 55.00 | 14.19 | 0.2275 | 0.8814 | 2.0943 | 0.4032 | 5.1943 | 16.4529 | 4.2462 | 5.7021 | 0.8814 | 1.1145 | 0.9750 | 0.9039 | 0.5983 | 2.5393 | 0.3938 | 0.4889 |
| 60.00 | 14.85 | 0.2193 | 0.8858 | 2.1666 | 0.3905 | 5.5483 | 17.6470 | 4.3685 | 6.1160 | 0.8858 | 1.1263 | 0.9849 | 0.8995 | 0.5882 | 2.6404 | 0.3787 | 0.4759 |
| 65.00 | 15.48 | 0.2120 | 0.8898 | 2.2360 | 0.3790 | 5.8996 | 18.8143 | 4.4820 | 6.5205 | 0.8898 | 1.1369 | 0.9939 | 0.8953 | 0.5789 | 2.7377 | 0.3653 | 0.4640 |
| 70.00 | 16.09 | 0.2054 | 0.8934 | 2.3030 | 0.3686 | 6.2484 | 19.9568 | 4.5879 | 6.9165 | 0.8934 | 1.1464 | 1.0021 | 0.8915 | 0.5702 | 2.8315 | 0.3532 | 0.4532 |
| 75.00 | 16.68 | 0.1994 | 0.8966 | 2.3678 | 0.3590 | 6.5950 | 21.0766 | 4.6871 | 7.3046 | 0.8966 | 1.1550 | 1.0098 | 0.8879 | 0.5620 | 2.9223 | 0.3422 | 0.4431 |
| 80.00 | 17.25 | 0.1939 | 0.8996 | 2.4305 | 0.3502 | 6.9395 | 22.1750 | 4.7804 | 7.6853 | 0.8996 | 1.1629 | 1.0169 | 0.8846 | 0.5544 | 3.0104 | 0.3322 | 0.4338 |
| 85.00 | 17.80 | 0.1889 | 0.9023 | 2.4914 | 0.3421 | 7.2822 | 23.2534 | 4.8684 | 8.0590 | 0.9023 | 1.1702 | 1.0236 | 0.8815 | 0.5471 | 3.0958 | 0.3230 | 0.4251 |
| 90.00 | 18.33 | 0.1843 | 0.9047 | 2.5505 | 0.3346 | 7.6232 | 24.3132 | 4.9517 | 8.4263 | 0.9047 | 1.1769 | 1.0298 | 0.8785 | 0.5403 | 3.1789 | 0.3146 | 0.4170 |
| 95.00 | 18.85 | 0.1800 | 0.9070 | 2.6081 | 0.3275 | 7.9626 | 25.3554 | 5.0308 | 8.7875 | 0.9070 | 1.1831 | 1.0357 | 0.8758 | 0.5338 | 3.2599 | 0.3068 | 0.4094 |
| 100.00 | 19.35 | 0.1760 | 0.9092 | 2.6643 | 0.3210 | 8.3006 | 26.3809 | 5.1060 | 9.1429 | 0.9092 | 1.1888 | 1.0413 | 0.8731 | 0.5276 | 3.3388 | 0.2995 | 0.4022 |

What is claimed is:

1. A device for defibrillating an atrium and/or a ventricle, said device having at least two capacitors which in the production of defibrillation pulses are discharged in a first phase involving a first configuration and in a successive second phase involving a different second configuration, wherein the device further has a means for switching that controls the discharge in the discharge phases of the first and second configurations so that the mean values of the voltages are substantially equal during the pulse durations for the first and second configurations and voltages below the rheobase do not occur in any of the discharge phases.

2. The device of claim 1 further comprising a means for switching that breaks off the discharge procedure of one of the first discharge phases in dependence on the ascertained discharge time constant—which is determined by capacitor and electrode resistance—upon the attainment of a predetermined tilt or the corresponding residual voltage or a discharge time duration which is to be expected and which was previously calculated on the basis of the ascertained time constant up to the attainment of the tilt or the corresponding residual voltage, and which correspondingly continues the discharge with a series connection of the capacitors with voltage doubling in a second phase.

3. The device of claim 1 wherein the first configuration involves switching means which control the discharge of an individual capacitor, the discharge of two parallel-connected capacitors or the sequential discharge of two individual capacitors.

4. The device of claim 3, further comprising means for switching which determine the discharge time constant in the first phase in the first configuration during the discharge.

5. The device of claim 4, further comprising means for switching which activate the individual discharge of a capacitor (one-capacitor system) instead of an individual or multi-capacitor system with predetermined time constants.

6. The device of claim 5, further comprising means for switching to discharge the residual voltage of at least one capacitor or a capacitor configuration in inverted mode.

7. The device of claim 6, further comprising means for switching to discharge the residual voltage of at least two capacitors in a parallel connection in inverted mode.

8. The device of claim 7 wherein the ascertained tilt or the corresponding residual voltage or the discharge time resulting therefrom is additionally variable by substantially plus/minus 20% as a function of the time constant.

9. The device of claim 2 wherein the first configuration involves switching means which control the discharge of an individual capacitor, the discharge of two parallel-connected capacitors or the sequential discharge of two individual capacitors.

10. The device of claim 9, further comprising means for switching which determine the discharge time constant in the first phase in the first configuration during the discharge.

11. The device of claim 10, further comprising means for switching which activate the individual discharge of a capacitor (one-capacitor system) instead of an individual or multi-capacitor system with predetermined time constants.

12. The device of claim 11, further comprising means for switching to discharge the residual voltage of at least one capacitor or a capacitor configuration in inverted mode.

13. The device of claim 12, further comprising means for switching to discharge the residual voltage of at least two capacitors in a parallel connection in inverted mode.

14. The device of claim 13 wherein the ascertained tilt or the corresponding residual voltage or the discharge time resulting therefrom is additionally variable by substantially plus/minus 20% as a function of the time constant.

15. A method for defibrillating an atrium and/or a ventricle with a device having at least two capacitors, the method characterized by the steps of first discharging the capacitors in a first phase involving a first configuration and then discharging the capacitors in a second phase involving a different second configuration, wherein the discharge in the at least two discharge phases is controlled in such a way that the mean value of the voltages in the discharge phases is substantially equal and does not fall below the rheobase in any of the discharge phases.

16. The defibrillation method of claim 15 wherein, in the first discharge phase, in dependence on the ascertained discharge time constant—which is determined by capacitor and electrode resistance—upon the attainment of a predetermined tilt or the corresponding residual voltage or a discharge time duration which is to be expected and which is previously calculated on the basis of the ascertained time constant until the attainment of the tilt or the corresponding residual voltage the procedure is broken off and discharge is correspondingly continued with a series connection of the capacitors with voltage doubling in the second phase.

17. The defibrillation method of claim 16 characterized in that the first phase involves the discharge of an individual capacitor, the discharge of two parallel-connected capacitors or the sequential discharge of two individual capacitors.

18. The defibrillation method of claim 17 characterized in that there are provided switching means which determine the discharge time constant in the first phase with the first configuration during the discharge.

19. The defibrillation method of claim 18 characterized in that, with predetermined impedance values, individual discharge of a capacitor is activated, instead of an individual or multi-capacitor system.

20. The defibrillation method of claim 19 characterized in that the residual voltage of at least one capacitor is discharged in inverted mode.

21. The defibrillation method of claim 20 characterized in that the residual voltage of at least two capacitors is discharged in inverted mode in parallel connection.

22. The defibrillation method of claim 21 characterized in that the ascertained tilt or the corresponding residual voltage is additionally varied by substantially plus/minus 20% as a function of the time constants RC1 or RC2.

* * * * *